United States Patent [19]

Sornein et al.

[11] Patent Number: 5,520,046

[45] Date of Patent: May 28, 1996

[54] PROCESS FOR THE CHEMICAL LOGGING OF A LIQUID AND CHEMICAL LOGGING INSTALLATION FOR PERFORMING SAID PROCESS

[75] Inventors: Jean-François Sornein, Pecqueuse; Jacques Delay, Sceaux; Remo Chiappini, L'Hay les Roses, all of France

[73] Assignee: Commissariat a l'Energie Atomique, Paris Cedex, France

[21] Appl. No.: 302,775

[22] PCT Filed: Mar. 18, 1993

[86] PCT No.: PCT/FR93/00271

§ 371 Date: Oct. 13, 1994

§ 102(e) Date: Oct. 13, 1994

[87] PCT Pub. No.: WO93/19354

PCT Pub. Date: Sep. 30, 1993

[30] Foreign Application Priority Data

Mar. 20, 1992 [FR] France ................................ 92 03381

[51] Int. Cl.$^6$ .......................... G01N 1/14; E21B 49/08
[52] U.S. Cl. .................... 73/151; 73/864.34; 73/864.73; 436/28; 166/264
[58] Field of Search ............................. 73/151, 152, 155, 73/864.81, 863.51, 863.41, 864.34, 863.71, 864.31, 864.73, 64.56; 106/264; 436/28, 30

[56] References Cited

U.S. PATENT DOCUMENTS

| | | | |
|---|---|---|---|
| 3,277,723 | 10/1966 | Bodman et al. ..................... | 73/864.62 |
| 3,430,497 | 3/1969 | Tenczar ............................... | 73/864.73 |
| 3,841,156 | 10/1974 | Wolfe .................................. | 73/864.73 |
| 3,930,754 | 1/1976 | Magg et al. ......................... | 166/264 |
| 4,160,622 | 7/1979 | Colburn .............................. | 166/264 |
| 4,295,801 | 10/1981 | Bennett ......................... | 73/864.73 X |
| 4,462,265 | 7/1984 | Rein .................................... | 73/863.33 |
| 5,224,389 | 7/1993 | Jensen et al. ....................... | 73/863.01 |

FOREIGN PATENT DOCUMENTS

| | | | |
|---|---|---|---|
| 0148696 | 7/1985 | European Pat. Off. . | |
| 2659748 | 9/1991 | France . | |
| 0146855 | 3/1981 | German Dem. Rep. .......... | 73/864.73 |
| 1169851 | 5/1964 | Germany . | |
| 3831549 | 3/1990 | Germany . | |

OTHER PUBLICATIONS

"Patent Abstracts of Japan", Takashi Kimoto, vol. 9, No. 281 (P–403)(2004), Nov. 8, 1985.

Primary Examiner—Michael J. Brock
Attorney, Agent, or Firm—Oblon, Spivak, McClelland, Maier & Neustadt

[57] ABSTRACT

The invention relates to a process for the chemical logging of a liquid and to an installation for performing the process. An object of the invention is to develop a process which makes it possible to carry out precise cartographies of chemical elements present in a liquid. This object is achieved with the aid of a process which includes performing a continuous sampling or removal of the liquid to be analyzed by way of a pipe moved progressively in the interior of the liquid. The pipe is provided with a pump which makes it possible to return the liquid to the surface, perform analyses on the samples and calculate for each analysis result the depth at which the sampling operation was carried out. The invention is more particularly used in boreholes, wells or oceanography.

16 Claims, 2 Drawing Sheets

_A_

_B_

PROCESS FOR THE CHEMICAL LOGGING OF A LIQUID AND CHEMICAL LOGGING INSTALLATION FOR PERFORMING SAID PROCESS

BACKGROUND OF THE INVENTION

1. Field of the Invention

The present invention relates to a process for chemical logging or diagraphy of a liquid, as well as to a chemical logging or diagraphy installation for performing said process. More specifically, said chemical logging process makes it possible to remove samples of liquid or water from a borehole, an ocean, a lake or a river and perform measurements thereon, in order to establish concentration profiles of at least one chemical element in said liquid. This process makes it possible to e.g. follow on a day to day basis the evolution of a pollution spill present in the ocean.

2. Discussion of the Related Art

In order to establish concentration profiles of chemical elements present in the water of a well or in the open water, the prior art already discloses a spot sampling procedure consisting of using a sampling bottle operated by a cable. These bottles are generally constituted by a cylinder open at its two ends and which is lowered to the requisite depth and remotely sealed. These bottles are sealed by an electrical or mechanical device. Thus, e.g. the sealing of the bottle can be obtained by means of a messenger, which is a type of counterweight or metal weight which is allowed to slide by gravity along the cable and which triggers the closing of a valve by its impact on a closing mechanism. The chemical measurements are subsequently performed in the laboratory on the samples taken. At present numerous bottle types exist meeting various demands with regards to the sampling volume, the materials forming the sampling bottle, the principle of initiating or triggering the same, the retention or not of the sampled dissolved gases, the filtration or the maximum pressure of use.

Such spot sampling processes take a long time to carry out, because it is a question of lowering and then raising again the said sampling bottle for each sample. In addition, in order to obtain a detailed concentration profile or for seeking a very localized anomaly, it is necessary to take a large number of samples.

A device is also known making it possible to perform multiple sampling operations and having on the same cable several sampling bottles designed so as to open and then close again in an automatic manner and simultaneously once the complete cable has been unrolled into the liquid mass to be analyzed.

Although this procedure speeds up the sampling operations it is not any more accurate, because the distance between two sampling bottles is frequently inadequate to obtain a very precise concentration profile or an anomaly passes through the reading made. Moreover, for a given sampling pass (i.e. the height over which the removal corresponding to a sample takes place), each sample is not necessarily representative of the mean concentration on the pass in question.

Finally, devices for in situ measurement are known comprising a specific probe for one or more chemical elements and which make it possible to perform a direct depth measurement at the sampling location and return the collected informations to the surface by means of an electric cable. These probes are e.g. spectral gamma probes for gamma emitters making it possible to e.g. measure iodine quantities.

However, these probes are generally very complex and costly, because they require the installation of an electronic device within a tight body and must be able to withstand pressure stresses. These probes are generally specific to one or several elements and their performance characteristics are limited. Finally, frequently, they are less accurate than a laboratory bench-type installation. The stresses to which said probes are exposed generally lead to a resolution loss and to interference phenomena.

SUMMARY OF THE INVENTION

To this end, the invention aims at obviating the aforementioned disadvantages and permitting the obtaining of precise chemical cartographies having one, two or three dimensions of a chemical element in a liquid, the water of a well or borehole or open water.

Therefore, the invention relates to a process for the chemical logging of a liquid making it possible to obtain a concentration profile of at least one chemical element in a liquid to be analyzed.

According to the features of the invention, this process comprises the stages consisting of:

performing a continuous sampling of said liquid to be analyzed by means of a pipe, whose inlet opening is progressively displaced in the mass or said liquid, said pipe being provided with means for sucking said liquid into the pipe and pumping means for raising the liquid within said pipe in the direction of the surface, carrying out on the surface analyses of the depth-sampled liquid using analysis means, permanently measuring and recording in simultaneous manner the length of a pipe immersed in the liquid, the flow rate of the liquid moving within said pipe and the elapsed time so that by knowing the dead volume of the pipe it is possible to bring about a correspondence with each given analysis value of the depth at which the sampling operation was performed.

Thus, in a single operation, i.e. by displacing the pumping point along the profile to be studied, this process makes it possible to take a number of samples. These samples are taken more rapidly than in the prior art. The repetition of this process makes it possible to perform chemical cartographies in two or three dimensions by displacing the starting point of the descent of the pipe.

Advantageously, within the pipe there is a turbulent liquid flow system. This significantly limits the dispersivity of the flow of the pumped liquid during its passage in the pipe.

Preferably, the ratio between the mean speed of the fluid circulating in the pipe and the displacement speed of the inlet opening of the pipe is between 4 and 100.

These values illustrate a relatively wide range of the speed ratios existing in practice. It should be noted that the more this ratio increases, the more the dispersivity is limited.

According to a first embodiment, the analysis of the sampled liquid takes place substantially in real time by at least one apparatus for the continuous analysis of a particular chemical element, said analysis being placed at the outlet of the pipe.

Thus, as in specific probes, this process makes it possible to obtain concentration profiles substantially in real time (simply delayed by the transit time of the liquid up to the surface) and guarantees the detection of variations and local anomalies which could escape the spot sampling operations.

In addition, with a single, relatively simple, basic sampling equipment, it is possible to then use all continuous laboratory measuring methods and equipments which are much more accurate. There is no need to carry out complex specific developments of the probes, as is the case when it is wished to realize a measurement probe in situ.

According to a second embodiment which can be performed in parallel with the first, the analysis of the sampled liquid takes place in delayed manner or with a time lag using at least one analysis apparatus on the basis of samples removed continuously at the pipe outlet on at least a fraction of the flow rate and in accordance with at least one sampling pass.

According to this process, when the liquid is sampled on a fraction of the flow rate, it is possible to retain part of the latter for real time analyses and another part for time lag-based analyses. Thus, when for a given chemical element, the continuous and real time measurement methods have a resolution or accuracy less satisfactory than time lag-based measurement methods, the linking of the two methods makes it possible to detect local anomalies by measurements performed in real time and simultaneously obtain precise values with a time lag. Moreover, as sampling takes place continuously, each sample is representative of the mean composition of the considered interval.

Finally and advantageously, there are several bypasses or derivations at the outlet of the pipe in order to perform a sampling operation in accordance with different passes.

Thus, this process makes it possible to rapidly carry out measurements on samples taken in accordance with relatively large sampling passes and then during the detection of an anomaly on a given sampling pass to then carry out more accurate analyses in said zone on samples with smaller passes removed in parallel.

The invention also relates to a chemical logging installation for performing the process described hereinbefore. According to the features of the invention, this apparatus comprises:

- a pipe having an inlet opening and provided with motor means making it possible to progressively displace it in the liquid mass to be analyzed,
- means for sucking the liquid to be analyzed, said suction means being located on the pipe and being able to inject the sucked up liquid into said pipe,
- pumping means located on said pipe and making it possible to raise to the surface the liquid in the pipe,
- means for supplying energy to the suction means and pumping means,
- means for the analysis of the collected liquid and located at the surface,
- means for measuring and recording as a function of time the position of the pipe inlet opening and
- means for measuring and recording as a function of time the flow rate of the liquid in the pipe.

BRIEF DESCRIPTION OF THE DRAWINGS

The invention is described in greater detail hereinafter relative to non-limitative embodiments and with reference to the attached drawings, wherein show.

DESCRIPTION OF THE PREFERRED EMBODIMENTS

Figure 1:
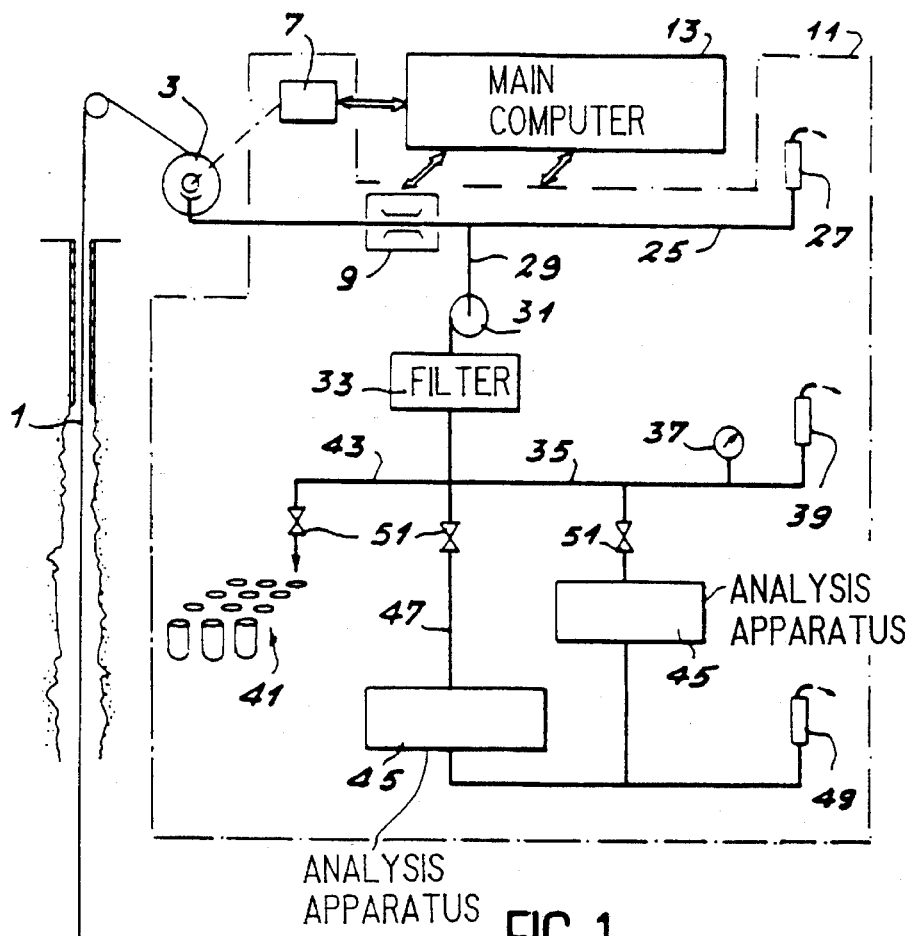
FIG. 1 a diagram constituting an overall view of the chemical logging installation making it possible to perform the process according to the invention.

The chemical diagraphy or logging installation will now be described in greater detail with reference to FIG. 1. This installation comprises a pipe 1 wound onto a winch 3, which is equipped with motor means making it possible to unwind or wind up the pipe 1 and therefore to lower or raise it within e.g. a well, as is shown in FIG. 1. The winch 3 also comprises a hydraulic rotary connector making it possible to connect the pipe 1 no a surface pipeline. This pipe 1 has at one of its ends an inlet opening 4 and is equipped with a sampling probe 5 positioned level with said inlet opening. The logging installation also comprises means 7 for measuring the length of pipe 1 immersed in the well, as well as an electromagnetic flowmeter 9 located at the outlet of the pipe 1.

Thus, the measuring means 7 make it possible to measure what in logging terms is referred to as the "depth reading", i.e. the position of the inlet opening 4 of the pipe 1. These measuring means 7 incorporate a pulley having a known circumference (metric pulley) driven by the pipe 1 and whose revolutions are counted by an optical coder. It would also be possible to use other depth measuring means such as a pressure gauge. Downstream of the flowmeter 9 are provided means for the analysis of the collected liquid, located on the surface, generally in a laboratory and referenced in general terms 11. The measuring means 7, flowmeter 9 and analysis means 11 are also connected to a main computer 13, as is diagrammatically illustrated by the double arrows. This computer 13 comprises an internal clock making it possible to measure and record the time (t).

The sampling probe 5 comprises a substantially cylindrical envelope 15 connected at its downstream or upper end to the pipe 1 by fixing means 17. Advantageously, the probe 5 has at its upstream or lower end an inlet filter 19, which is not generally necessary when sampling operations are performed in the ocean. Within said envelope 15 are provided at least one pump 21 and in the represented embodiment three interconnected pumps.

Each pump 21 simultaneously fulfils the suction function of the liquid 23 in which the sampling probe 5 is immersed and the pumping function making it possible to raise the liquid 23 sucked into the pipe 1 up to the surface where said liquid will be subsequently analyzed. Suction takes place at the inlet opening 4 of the probe or more specifically its inlet filter 19.

The pump or pumps 21 are supplied by means e.g. constituted by internal batteries, or from the surface by a cable, or in the preferred embodiment, by a single cable combining the functions of the pipe 1, the carrier cable and the electric supply cable. In this case, the hydraulic connector of the winch 3 is also electrical. For reasons of simplification in FIG. 1, said cable or pipe 1 has been diagrammatically represented.

The sampling probe 5 will not be described in greater detail, because on the one hand its characteristics in no way limit the invention and on the other because an expert could easily realize such a probe making it possible to take the desired samples.

In the embodiment described hereinbefore, the liquid pumping and suction means are combined into one and the same pump 21 located within the sampling probe 5. However, in variants not shown in FIG. 1, it would be possible to subdivide the pump 21 into two parts, a first part permitting the suction of the liquid 23 to be analyzed in order to inject it into the pipe 1 and a second part making it possible to raise to the surface the liquid 23 in said pipe 1. In this case, it would also be possible to place the pumping part, on the surface and the suction part in the water, at the end 4 of the pipe 1.

Moreover, in the preferred embodiment of the invention, the sampling probe 5 is placed at the end of the pipe 1. However, it would also be possible to place said probe 5 on a median part of the pipe 1, or even on the surface. Only the pipe 1 would then move in the profile to be analyzed.

As illustrated in FIG. 1, the means 11 for the analysis of the collected liquid incorporate a pipeline 25 connecting the outlet of the flowmeter 9 to a control or check flowmeter 27. A pipeline 29, forming a bypass from the pipeline 25 connects the latter to a pump 31 making it possible to place the liquid under pressure again before passing it to the other equipments. A filter 33 is positioned in series downstream of said pump 31. A pipeline 35 connects said filter 33 to a control or check pressure gauge 37 and then to a second control or check flowmeter 39. A sampling apparatus 41 is connected by a bypass 43 to the pipeline 35. An apparatus 45 for analyzing the concentration of the sought chemical element is also connected by a bypass 47 to the pipeline 35. This analysis apparatus 45 is also connected to a third control or check flowmeter 49. Flow regulating valves 51 are respectively provided between the sampling apparatus 41 or the analysis apparatus 45 and the pipeline 35.

As illustrated in FIG. 1, it would be possible to provide two apparatuses 45 for analysing the concentration of given chemical elements. However, the number of sampling apparatuses 41 or analysis apparatuses 45 is not a limitative feature of the invention.

During its transportation into the installation, the water sampled at an initial in situ pressure is firstly subject to an overpressure (in the case of an immersed pumping) and is then progressively brought to atmospheric pressure, or even to an underpressure if the apparatus operates by suction. This progressive pressure drop, accompanied by flow turbulence is advantageous for the degassing of gases which may be dissolved in the sampled water.

In a not shown embodiment, it would also be possible to install a system for collecting and sampling said gases on the surface (gas recovery bell and transfer system).

The use of said chemical logging installation, as well as the process according to the invention will now be described in greater detail.

Contrary to what happened in the prior art, the process according to the invention consists of carrying out a continuous sampling of the liquid 23 to be analyzed, while progressively moving (generally at a constant speed) within the liquid 23, the pipe 1, whose end is provided with the sampling probe 5. Generally said sampling takes place on a vertical profile and in this case the pipe 1 and the probe 5 are moved vertically from top to bottom, so that the liquid 23 is sampled "at rest". Thus, if sampling takes place from bottom to top, the sampled liquid 23 may have been stirred up as a result of the passage of the pipe. Nevertheless, in certain specific cases, it would be possible to carry out a sampling operation by again raising the probe 5. Thus, in an untubed well, the descent of a probe at a regular speed is sometimes thwarted by the fact that the probe is placed on irregularities of the wall, whereas the raising of the probe again causes no problems.

In general terms, the profile can be vertical, inclined or even horizontal and the apparatus can be towed at a constant depth behind e.g. a ship. In addition, said profile is not necessarily rectilinear.

The liquid 23 sucked up by the sampling probe 5 is returned within the pipe 1 to the surface towards the flowmeter 9 and the analysis means 11.

Using the measuring means 7, a measurement takes place of the position of the inlet opening 4 of the pipe 1 when the probe 5 is lowered into the interior of the well. As a result of the time differential with respect to said information, the movement speed Vd of the inlet opening 4 is obtained. A measurement also takes place of the average speed V1 of the displacement of the liquid 23 within the pipe 1 using the flowmeter 9. Finally, a measurement takes place of the dead volume of the pipe 1, which is a constant value for a given installation. The pipe 1 is permanently filled with liquid even when no measurement takes place. When the pipe 1 is immersed in the liquid 23 and the measurements are started, the first operation consists of raising into the analysis means 11 a liquid volume initially present in said pipe and called the dead volume and whose value corresponds to the product of the section of the pipe by its length.

All these measurements make it possible to bring about correspondence with each given analysis value for a given sample, the depth at which the said sample is taken. The calculations are generally performed by the computer 13, which permanently performs the recording of the data supplied by the measuring means 7 (depth reading), by the flowmeter 9 and by the analysis means 11, as well as the determination of the sample reading corresponding to the analysis during the time (t). In order to determine said reading, the working time ($\Delta t$) is calculated in the apparatus as a function of the flow rates effectively recorded in the period preceding the analysis and the reading occupied by the end of the pipe at the time (t–$\Delta t$) is sought on the basis of the recorded depth readings.

The quality of the results obtained is dependent on the one hand of the dispersivity of the flow in the pipe 1 between the sample removal point and the analysis and/or sampling point and on the other hand the sampling coefficient.

It has been observed that the dispersivity of the flow of liquid rising in the pipe 1, during the passage thereof, tends to entrain a mixture of waters having a neighboring origin and introduce a smoothing of the chemical profile obtained compared with the real chemical profile. This dispersivity function is mainly dependent on the flow conditions within the pipe 1 and on the length of the latter.

The influence of the flow conditions has been revealed by laboratory tests consisting of measuring the dilution undergone by a tracer square wave pulse flowing in a pipe, for different pipe diameters and for different flow conditions. The results shown in FIG. 2 were obtained for a pipe length of 100 m, a length of the tracer square wave pulse introduced at the start 80 cm at a concentration C0, a maximum measured concentration at the outlet C1 and soft (non salt) water at 20° C.

Figure 2:
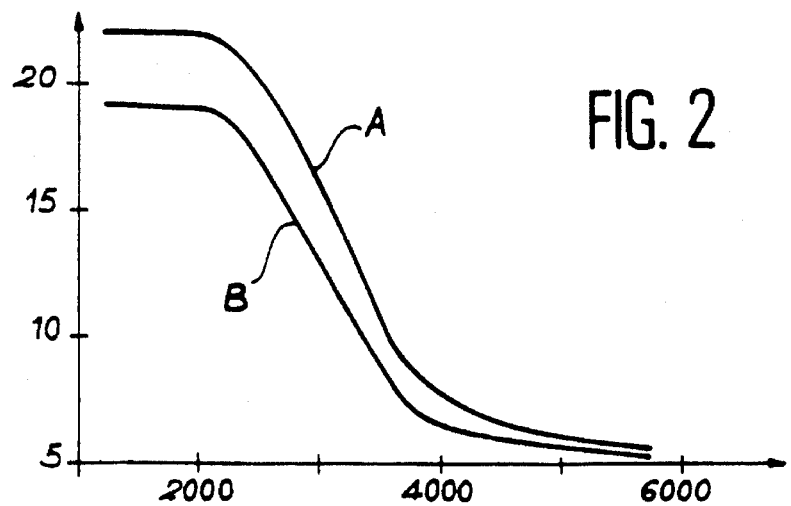
FIG. 2 a graph illustrating the dilution of a tracer square wave pulse following the circulation along a 100 m pipe as a function of the Reynolds number of the flow.

FIG. 2 shows on the abscissa the Reynolds number (Re=VfxDx ($\rho/\mu$), with Vf equal the mean speed of the fluid in the pipe, D equals the pipe diameter, $\rho$ equals the fluid density and $\mu$ the fluid viscosity. This nondimensional quantity indicates the type of flow: laminar (Re <2000), turbulent hydraulically smooth (4000 <Re <100,000) or intermediate.

On the ordinate is given the dilution corresponding to C0/C1. Curve A corresponds to the results obtained for a diameter 6 mm pipe and curve B to a 4 mm diameter pipe. The dispersivity of the flow revealed by the dilution of the experimental square wave pulse is great under laminar flow conditions, but limited under turbulent conditions. Consequently, it is preferable to have within the pipe 1 a turbulent flow condition system, so as to avoid said dispersivity. This turbulent flow will be obtained by the correct dimensions of the pipe 1 or by adapting the characteristics of the pumping means 21. It should be noted that for a given pipe diameter and flow rate, as well as for a constant density to viscosity ratio, the dispersivity increases with the pipe length. The sampling coefficient is defined by the ratio between the mean movement speed V1 of the sucked in liquid 23 flowing within the pipe and the movement speed Vd of the inlet opening 4 of the pipe 1. The increase in the sampling coefficient (by the decrease of −Vd or the increase of V1), limits the dispersivity. In practice, the reduction of Vd is limited by the length of the profile to be analyzed and by the time which it is wished to devote to the measurement, whereas the increase of V1 is linked with the pumping means. For example, under "normal" operating conditions, Vd can vary between 1 and 10 m per min. and V1 between 40 and 100 m per min. Consequently, said sampling coefficient is between 4 and 100.

The spatial resolution is subsequently optimized by the computer 13 by adjusting said parameters and by mathematically treating the data (deconvolution).

In a purely illustrative manner and for an application requiring a pipe length of 600 meters, the following values were evaluated and then tested in the laboratory and in situ (over a depth of 600 m in the well) in order to have simultaneously a low dispersivity and a good sampling coefficient:

internal pipe diameter: 4 mm, flow rate within the pipe: approx. 15 cm$^3$/s corresponding to a movement speed of the liquid within the pipe of approximately 1 m/s, injection pressure of the pump 21: $40.10^5$ Pa, displacement speed of the pipe inlet opening: 10 cm/s, Reynolds number of the flow: 5000.

In this case a sampling coefficient of 10 is obtained.

Figure 3:
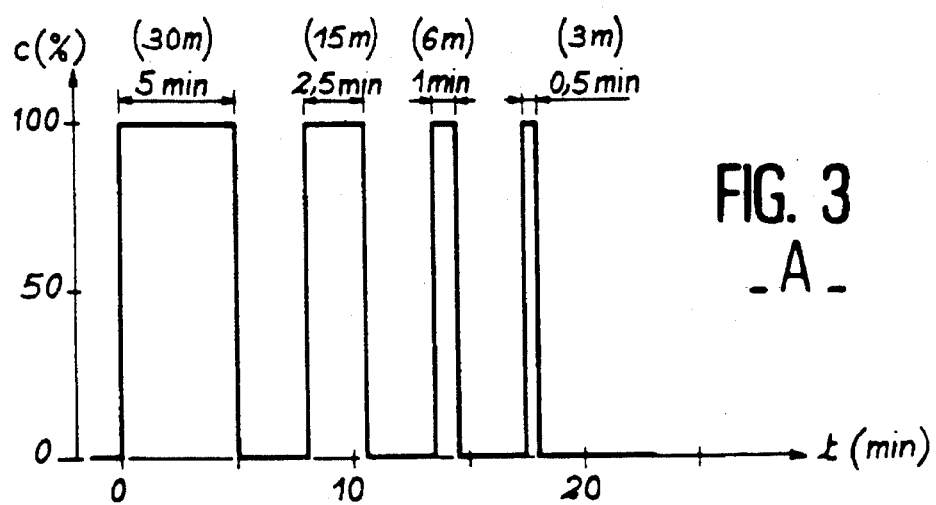
FIGS. 3A and B the results of a resolution test.
Figure 3:
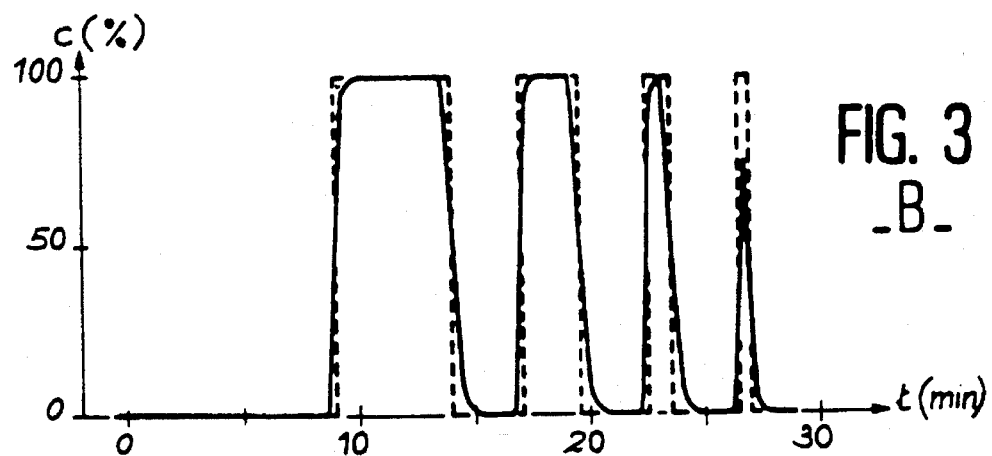

Spatial resolution tests under these conditions are shown in FIGS. 3A and 3B. At the inlet of the device marker square wave pulses were injected for different times (5, 2.5, 1 and 0.5 minutes) corresponding to a pipe opening displacement length of respectively 30, 15, 6 and 3 meters. The original concentration is 100% (cf. part A of FIG. 3). The concentration signal is then observed on leaving the apparatus (cf. part B in FIG. 3, continuous line signal). The output signal is time-displaced (mean transit time in the pipe: 9 minutes). It can be seen that the first three marker square wave pulses (lasting at least one minute) have at the outlet their original concentration. The 30 second square wave pulse reaches at the apparatus outlet a maximum concentration equal to 70% of its original concentration. It is thus found that even a local anomaly (pollution) over a few meters can be detected.

It has been found that when the pipe diameter is below 4 mm, there are considerable pressure drops and it is necessary to use a more powerful pump and therefore possibly more voluminous and/or more costly. Moreover, when the pipe length exceeds 600 m, it is also necessary to have a larger pump or a slower pipe descent speed. In addition, the overall dimensions on the winch would increase.

After carrying out the sampling operations, it is then possible to analyzed the sampled liquid. This analysis can take place either in real time, or with a time lag. In the case of a real time analysis, an analysis apparatus 45 is positioned in series on the pipeline 25 bringing the liquid collected in the pipe 1. It is possible to carry out a measurement on only part of the flow and release to the exterior the remainder of the sampled liquid. The type of analysis apparatus is a function of the nature of the chemical element which it is wished to analyze. For illustration only, said analysis apparatus can comprise a fluorimeter, specific electrodes of ions or an apparatus for measuring the conductivity (salinity).

When the analysis takes place with a time lag, it is necessary to take samples at the outlet of the pipe 1 using a sampling apparatus 41, which makes it possible to take samples in accordance with a given sampling pass. In other words, at the outlet of the pipe 1 is taken a given liquid volume corresponding to a liquid height 23 in the analyzed liquid column. For example, in a 600 m deep well, it is possible to take 20 samples corresponding to the liquid volume or to part of the latter collected over a depth of 30 m. On a bypass of the pipe 1 it is also possible to carry out a sampling operation with a different pass. For example, it is possible to take 40 samples corresponding to 15 m of the liquid column to be analyzed. Thus, it is possible to carry out a first analysis on all the first 20 samples and when an anomaly has been detected corresponding to a given depth, an analysis of a more precise nature is performed on certain of the 40 samples corresponding to a water column height of only 15 m.

Figure 4:
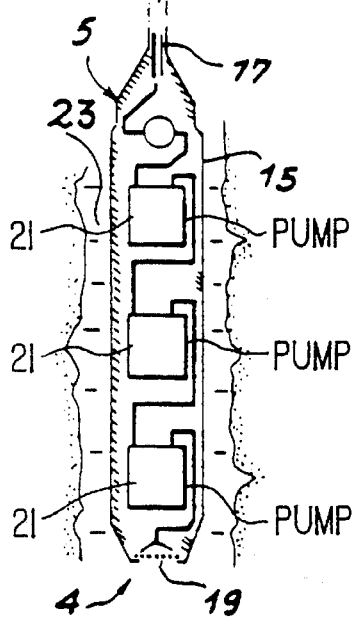
FIG. 4 a theoretical curve illustrating an example of the results which it is possible to obtain with the chemical logging installation according to the invention.
Figure 4:
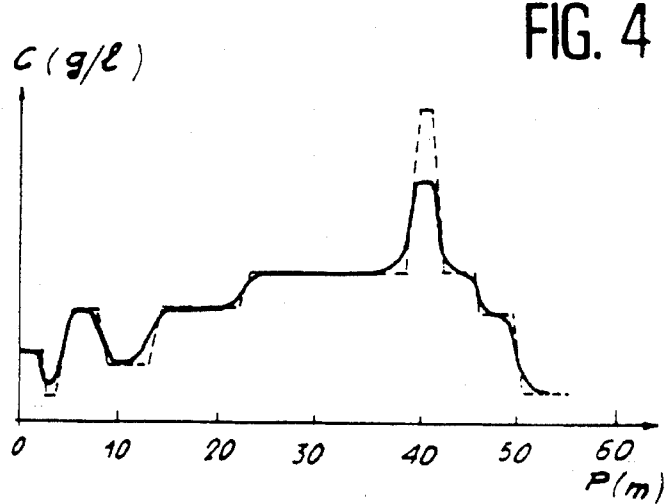

FIG. 4 illustrates a theoretical curve example obtainable by the process according to the invention and representing the concentration (C) of a product as a function of the sampling depth (P).

It is possible to see a continuous line curve corresponding to the measured profile and a mixed line curve corresponding to the real profile. Thus, there is a certain smoothing of the values, but an anomaly can still be accurately detected. Here, for example it is possible to observe a peak, which is certainly smaller than the real peak, at between 30 and 40 m depths. The technician can then recommence a series of measurements at the level of these values or use samples having a smaller pass.

It is also possible with this installation and process to measure liquid circulation speeds in situ by following a tracer, e.g. a chemical or colored tracer. The apparatus according to the invention can also be used for putting the tracer in place by injection from the surface. The apparatus must then be slightly modified.

We claim:

1. A process for chemical logging of a liquid which makes it possible to obtain a concentration profile of at least one chemical element in a liquid to be analyzed, the process comprising the steps of:

carrying out a continuous sampling of said liquid to be analyzed by means of a pipe, the pipe having an inlet opening which is progressively moved into a mass of said liquid, said pipe being provided with means for sucking the liquid into the pipe and pumping means for raising said liquid within said pipe, in the direction of a surface;

performing on the surface analyses of the depth-sampled liquid using analysis means; and permanently measuring and simultaneously recording a length of the pipe immersed in the liquid, a flow rate of the liquid moving within the pipe and a time, so that by knowing a dead volume of the pipe it is possible to bring about correspondence with each given analysis value of a depth at which sampling took place.

2. A process for the chemical logging of a liquid according to claim 1, wherein within the pipe turbulent liquid flow conditions prevail while the liquid is being sucked within the pipe and the liquid is being raised within the pipe.

3. A process for the chemical logging of a liquid according to claim 1, wherein the inlet opening of the pipe is moved vertically and from top to bottom in the liquid to be analyzed.

4. A process for the chemical logging of a liquid according to claim 1, wherein a ratio between a mean speed of the liquid flowing in the pipe, obtained by measuring the flow rate and a movement speed of the inlet opening of the pipe and obtained on the basis of the measurement of the length of the pipe immersed in the liquid, is between 4 and 100.

5. A process for the chemical logging of a liquid according to claim 1, wherein the analysis of the sampled liquid takes place substantially in real time by at least one apparatus for the continuous analysis of a particular chemical element, said apparatus being placed at an outlet of the pipe.

6. A process for the chemical logging of a liquid according to claim 1, wherein the analysis of the sampled liquid takes place in delayed manner, using at least one analysis apparatus, on the basis of samples taken continuously at an outlet of the pipe on at least one fraction of the flow rate and according to at least one sampling pass.

7. A process for the chemical logging of a liquid according to claim 6, wherein there are several bypasses at the outlet of the pipe in order to carry out sampling using different passes.

8. An installation for chemical logging of a liquid, the installation comprising:

a pipe having an inlet opening and provided with motor means providing, while logging, progressive movement thereof in a liquid mass to be analyzed;

means for sucking the liquid to be analyzed, said suction means being located on the pipe and making it possible to inject the sucked in liquid into said pipe;

pumping means, located on said pipe which makes it possible to raise to a surface the liquid in the pipe;

means for supplying with energy the suction means and the pumping means;

means for analyzing the collected liquid and located on the surface;

means for measuring and recording as a function of time a position of the inlet opening of the pipe; and means for measuring and recording as a function of time a flow rate of the liquid within the pipe.

9. An installation for the chemical logging of a liquid according to claim 8, wherein dimensions of the pipe or the characteristics of the pumping means are designed so as to have within the pipe turbulent flow conditions.

10. An installation for the chemical logging of a liquid according to claim 8, wherein the suction means and the pumping means coincide and are placed within a sampling probe.

11. An installation for the chemical logging of a liquid according to claim 10, wherein the sampling probe is fixed to the inlet opening of the pipe.

12. An installation for the chemical logging of a liquid according to claim 11, wherein the sampling probe comprises at least one filter located at an entrance of the probe.

13. An installation for the chemical logging of a liquid according to claim 10, wherein the analysis means for the collected liquid incorporate at least one apparatus for the continuous analysis of a concentration of a chemical element in the liquid to be analyzed, said apparatus being placed at an outlet of the pipe.

14. An installation for the chemical logging of a liquid according to claim 8, wherein the means for analyzing the collected liquid incorporate at least one apparatus for sampling the collected liquid, in accordance with at least one predetermined sampling pass.

15. An installation for chemical logging of a liquid according to claim 8, wherein the means for analyzing the collected liquid incorporate at least one apparatus for the continuous analysis of a concentration of a chemical element in the liquid to be analyzed, said apparatus being placed at an outlet of the pipe.

16. An installation for the chemical logging of a liquid according to one of claims 15 or 13, further comprising a computer connected to the means for measuring the position of the inlet opening of the pipe, to the means for measuring the flow rate of the liquid within the pipe and to the analysis means, making it possible to associate with each sample or liquid portion passing into the analysis apparatus, a depth at which sampling took place.

* * * * *